(12) United States Patent
Yokoyama et al.

(10) Patent No.: US 7,791,035 B2
(45) Date of Patent: Sep. 7, 2010

(54) ELECTRONIC CASSETTE TYPE OF RADIATION DETECTION APPARATUS

(75) Inventors: Keigo Yokoyama, Honjo (JP); Tadao Endo, Honjo (JP); Toshio Kameshima, Kumagaya (JP); Tomoyuki Yagi, Honjo (JP); Katsuro Takenaka, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/713,389

(22) Filed: Feb. 26, 2010

(65) Prior Publication Data

US 2010/0148077 A1 Jun. 17, 2010

Related U.S. Application Data

(62) Division of application No. 11/765,124, filed on Jun. 19, 2007, now Pat. No. 7,696,484.

(30) Foreign Application Priority Data

Aug. 29, 2006 (JP) .............................. 2006-232349
Jun. 8, 2007 (JP) .............................. 2007-152707

(51) Int. Cl.
  *H01L 27/146* (2006.01)
(52) U.S. Cl. ................................. 250/370.09
(58) Field of Classification Search ...............................
  250/370.01–370.15; 378/98.8
  See application file for complete search history.

(56) References Cited

U.S. PATENT DOCUMENTS

| | | | | |
|---|---|---|---|---|
| 5,282,236 | A * | 1/1994 | Hayes et al. ................. | 378/182 |
| 6,952,015 | B2 | 10/2005 | Kameshima ........... | 250/370.11 |
| 6,952,464 | B2 | 10/2005 | Endo ....................... | 378/98.11 |
| 6,985,555 | B2 | 1/2006 | Endo ....................... | 378/98.11 |
| 7,002,157 | B2 | 2/2006 | Kameshima ........... | 250/370.11 |
| 7,012,260 | B2 | 3/2006 | Endo ....................... | 250/370.11 |
| 7,075,088 | B2 | 7/2006 | Watanabe et al. ...... | 250/370.01 |
| 7,138,639 | B2 | 11/2006 | Kameshima ........... | 250/370.11 |
| 7,154,099 | B2 | 12/2006 | Endo ....................... | 250/370.11 |
| 7,227,926 | B2 | 6/2007 | Kameshima et al. ....... | 378/98.9 |
| 7,564,038 | B2 | 7/2009 | Endo et al. .............. | 250/370.11 |
| 7,629,587 | B2 | 12/2009 | Yagi et al. .............. | 250/370.15 |
| 2003/0223540 | A1 * | 12/2003 | Hayashida et al. ......... | 378/98.8 |
| 2004/0252613 | A1 | 12/2004 | Iwakiri .................... | 369/53.12 |
| 2005/0067579 | A1 | 3/2005 | Tsuchiya et al. ........ | 250/370.15 |
| 2005/0109927 | A1 | 5/2005 | Takenaka et al. ......... | 250/252.1 |
| 2005/0199834 | A1 | 9/2005 | Takenaka et al. ............ | 250/580 |
| 2005/0200720 | A1 | 9/2005 | Kameshima et al. ..... | 348/220.1 |

(Continued)

FOREIGN PATENT DOCUMENTS

JP 2003-248060 9/2003

(Continued)

*Primary Examiner*—David P Porta
*Assistant Examiner*—Kiho Kim
(74) *Attorney, Agent, or Firm*—Fitzpatrick, Cella, Harper & Scinto

(57) ABSTRACT

An electronic cassette type of radiation detection apparatus having a sensor array including a plurality of sensors for detecting incident radiation has a connecting portion to which detachable additional function modules are connected. A selection unit is provided for changing a radiographing mode from a still image radiographing mode and a moving image radiographing mode into a selectable state in response to a connection of at least one of the additional function modules changes.

17 Claims, 6 Drawing Sheets

U.S. PATENT DOCUMENTS

| | | | |
|---|---|---|---|
| 2005/0220269 A1 | 10/2005 | Endo et al. | 378/114 |
| 2005/0228273 A1 | 10/2005 | Tamakoshi | 600/425 |
| 2005/0264665 A1 | 12/2005 | Endo et al. | 348/308 |
| 2006/0017028 A1 | 1/2006 | Ohara et al. | 250/580 |
| 2006/0119719 A1 | 6/2006 | Kameshima | 348/308 |
| 2006/0192130 A1 | 8/2006 | Yagi | 250/370.14 |
| 2006/0289774 A1 | 12/2006 | Endo et al. | 250/370.09 |
| 2007/0034806 A1* | 2/2007 | Hornig | 250/370.08 |
| 2007/0040099 A1 | 2/2007 | Yokoyama et al. | 250/208.1 |
| 2007/0069144 A1 | 3/2007 | Kameshima | 250/370.09 |
| 2007/0080299 A1 | 4/2007 | Endo et al. | 250/370.09 |
| 2007/0096032 A1 | 5/2007 | Yagi et al. | 250/370.11 |
| 2007/0125952 A1 | 6/2007 | Endo et al. | 250/369 |
| 2007/0131843 A1 | 6/2007 | Yokoyama et al. | 250/205 |
| 2007/0183573 A1 | 8/2007 | Kameshima et al. | 378/98.9 |
| 2007/0210258 A1 | 9/2007 | Endo et al. | 250/370.09 |
| 2007/0290143 A1 | 12/2007 | Kameshima et al. | 250/370.09 |
| 2007/0291904 A1 | 12/2007 | Takenaka et al. | 378/207 |
| 2007/0297567 A1 | 12/2007 | Takenaka et al. | 378/98.2 |
| 2008/0011958 A1 | 1/2008 | Endo et al. | 250/370.08 |
| 2008/0013686 A1 | 1/2008 | Kameshima et al. | 378/98 |
| 2008/0029688 A1 | 2/2008 | Yagi et al. | 250/208.1 |
| 2009/0001276 A1 | 1/2009 | Yagi et al. | 250/370.09 |
| 2009/0294679 A1 | 12/2009 | Yagi et al. | 250/370.09 |
| 2010/0046711 A1 | 2/2010 | Kameshima et al. | 378/114 |

FOREIGN PATENT DOCUMENTS

| | | |
|---|---|---|
| JP | 2005-013310 | 1/2005 |
| JP | 2005-308440 | 11/2005 |

* cited by examiner

ELECTRONIC CASSETTE TYPE OF RADIATION DETECTION APPARATUS

RELATED APPLICATIONS

This application is a divisional of patent application Ser. No. 11/765,124, filed Jun. 19, 2007, claims benefit of the filing date of that application under 35 U.S.C. §120, and claims priority benefit under 35 U.S.C. §119 of Japanese Patent Applications Nos. 2006-232349, filed Aug. 29, 2006, and 2007-152707, filed Jun. 8, 2007; the entire contents of each of the three mentioned prior applications are hereby incorporated by reference herein.

BACKGROUND OF THE INVENTION

1. Field of the Invention

The present invention relates to a radiation detection apparatus, and in particular, to a mobile electronic-cassette radiation detection apparatus.

2. Description of the Related Art

An X-ray image has been digitized in a hospital in recent years. A flat type of digital X-ray radiographing apparatus (hereinafter referred to as flat panel detector (FPD)) has been used instead of film. In addition to a stationary type of FPD, the FPDs include an electronic cassette type which is mobile and easier to handle than the stationary type, as described in Japanese Patent Application Laid-Open Nos. 2003-248060 and 2005-013310.

There has been a demand for a lighter FPD with desired functions.

SUMMARY OF THE INVENTION

A conventional mobile electronic cassette type of radiation detection apparatus, however, is only capable of photographing a still image. A cassette type of radiation detection apparatus has been desired which is capable of photographing a moving image.

The present invention has its purpose to provide a mobile electronic cassette type of radiation detection apparatus which weighs little, has functions which can be selected at discretion and is adapted to moving image photographing.

To achieve the above purposes, an electronic cassette type of radiation detection apparatus according to the present invention has a sensor array including a plurality of sensors for detecting incident radiation and a connection portion to which a detachable additional function module is connected, wherein a selection unit is provided for changing a radiographing mode from a still image radiographing mode and a moving image radiographing mode into a selectable state in response to connection to at least one additional function module.

The present invention provides an electronic cassette type of radiation detection apparatus adapted to moving image photographing in which a user can select necessary functions at discretion.

Detaching the additional function modules from the electronic cassette type of radiation detection apparatus makes the apparatus lighter, providing an electronic cassette type of radiation detection apparatus which is easier to carry and handle.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

An exemplary embodiment for carrying out the present invention is described in detail below with reference to the drawings.

The embodiments of the electronic cassette type of radiation detection apparatus according to the present invention are described below. In the present specification, the electronic cassette type refers to a mobile radiation detection apparatus for radiography. Radiation includes X-rays, alpha rays and gamma rays. In the following embodiments, in particular, the electronic cassette type of X-ray detecting apparatus is described, but this does not limit the present invention.

First Embodiment

The first embodiment of the electronic cassette type of X-ray detecting apparatus (electronic cassette) according to the present invention is described below.

Figure 1:
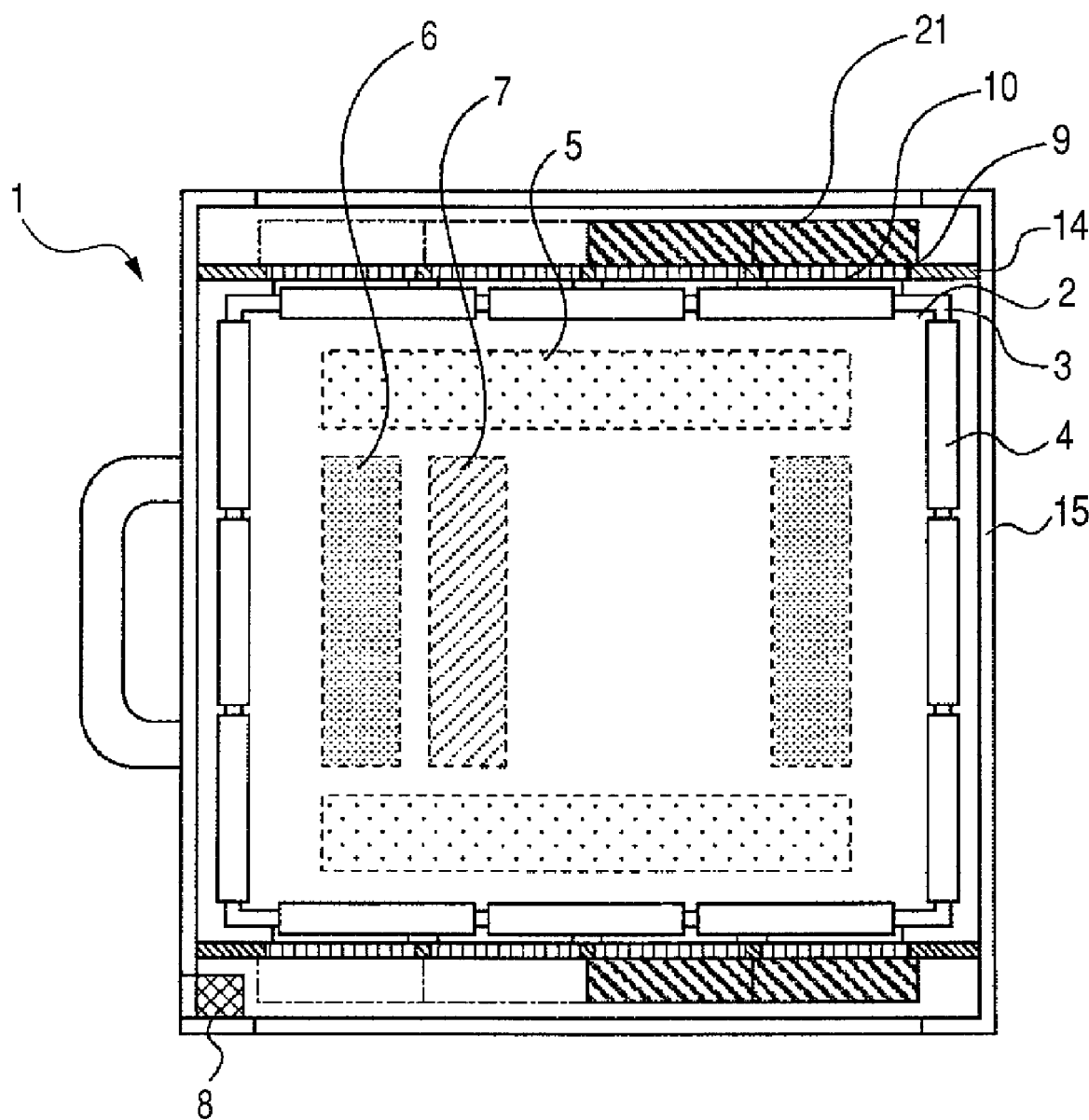
FIG. 1 is a cross section of an X-ray detecting apparatus in the first embodiment of the present invention.

FIG. 1 is a cross section illustrating the structure of the electronic cassette in the present embodiment, viewed from the X-ray incident side. As illustrated in FIG. 1, a base plate 3 to which a sensor panel 2 is fixed is fastened to a casing 15. The sensor panel 2 is connected to a flexible printed circuit 4. The flexible printed circuit 4 is connected to a driving circuit 5 or a reading circuit 6 arranged on the side opposite to the sensor panel 2 of the base plate 3. The reading circuit 6 is connected to a memory 8 being a storage device by a wiring (not shown). An analog signal read out from the sensor panel 2 is converted to a digital signal by the reading circuit 6 and stored into the memory 8. A control circuit 7 for operating the driving circuit 5, reading circuit 6 and memory 8 is connected thereto by a wiring (not shown). The control circuit 7 is capable of synchronizing radiation exposure with the operation of the driving circuit 5 and the reading circuit 6. The electronic cassette has a connecting terminal 9 being a connecting portion for connecting the electronic cassette 1 to an additional function module 21. The additional function module 21 is connected to one of the driving circuit 5 and the reading circuit 6 through a connection wiring 10. A battery (not shown) is disposed inside the electronic cassette 1, permitting the electronic cassette 1 to be operated without a cable. It is to be understood that the electronic cassette 1 may be operated with a cable connected, without disposing a battery in the casing. This is the basic configuration of the electronic cassette 1 in the first embodiment which is easy to carry and handle and capable only of radiographing a still image. The connection of the additional function modules 21 to the electronic cassette 1 adds a moving-image radiographing mode to the radiographing mode of the electronic cassette 1 in addition to a still-image photographing mode. That is, a radiographing mode is changed a still image radiographing mode and a moving image radiographing mode into a selectable state. The addition of the additional function modules 21 makes the performance of the electronic cassette 1 desirable for moving image radiographing. In addition, it is desirable that the connection of at least one of the additional function modules changes a radiographing mode from a mode where only a still image can be radiographed to a mode where a moving image can be radiographed.

It is also suitable, to make it easy to use the electronic cassette 1, that the electronic cassette 1 automatically changes in the radiographing mode depending upon whether or not the additional function modules 21 are connected to the basic configuration, as described below. For the automatic change of the radiographing mode, in the basic configuration, only a still image can be radiographed. Connecting at least one of the additional function modules 21 changes the radiographing mode from the still-image radiographing mode to the moving-image radiographing mode. For this reason, detaching all the additional function modules 21 from the electronic cassette 1 automatically changes the radiographing mode from the moving-image radiographing mode to the still-image radiographing mode. A control circuit operates as a selection unit for changing a radiographing mode from a still image radiographing mode and a moving image radiographing mode into a selectable state.

In X-ray radiographing by using the electronic cassette 1 with the basic configuration, the electronic cassette 1 is connected to an external computer to confirm images and transfers signals stored in the memory 8 thereto. Only the memory 8 can be made detachable to be connected to an external computer. Signals are therefore processed in the external computer and images are displayed on an external display.

The additional function modules 21 can be additionally connected to the electronic cassette 1 with the basic configuration. The additional function modules 21 include, for example, a storage device, image processing circuit, display, wireless communication circuit, light source, cooling element, heat radiator plate and battery. At least one of these additional function modules 21 is properly combined to be connected to the electronic cassette 1, allowing radiographing a moving image and extending the time period for the moving image radiographing. Thus, when a moving image is not radiographed, the electronic cassette 1 can be reduced in weight, and when the additional function modules 21 are connected, a moving image can be radiographed. FIG. 1 illustrates a configuration in which eight additional function modules 21 are connected. The figure illustrates four out of eight additional function modules 21. In the present embodiment, a partitioning wall 14 is arranged between the areas where the sensor panel 2 and the additional function modules 21 are disposed. The partitioning wall 14 can prevent dust and moisture from entering the sensor panel 2 from the outside, with improved reliability of the electronic cassette 1. Examples of the additional function modules connected to the electronic cassette 1 are described below.

The connection of the storage device to the electronic cassette 1 enables increasing capacity for storing signals. For example, a memory or hard disk can be used. The connection of the storage device to the electronic cassette 1 with the basic configuration enables to increase the number of radiographed images and extend a radiographing time-period. This is desirable particularly for the moving image radiographing.

By connecting, to the electronic cassette, an additional circuit of a reading circuit 6 provided with an AD (analog to digital) converter for converting an analog signal to a digital signal, the conversion can be accelerated. And, by connecting, to the electronic cassette, an additional circuit of a reading circuit 6 provided, a signal from the sensor panel 2 of a fundamental structure can be subjected to a parallel processing by the reading circuit 6 and a signal processing circuit. In case that two or more AD converters are arranged in the reading circuit of the fundamental structure, if the signal processing circuit is provided with the same number of AD converters as ones in the signal reading circuit 6, higher speed of the processing can be achieved. Accordingly, the configuration of the present embodiment is suitable for the moving image radiographing in which high speed inputting of analog signal is necessary. Moreover, when the reading circuit 6 is provided with a low noise AD converter and a signal processing circuit of low driving speed most suitable for the still image radiographing and the signal processing circuit is provided with AD converter and a signal processing circuit of high driving speed, a digital signal suitable for the moving image can be derived.

The connection of the image processing circuit to the electronic cassette 1 enables to correct a signal transferred from the reading circuit 6. For example, the image processing circuit performs a fixed pattern noise correction, defect correction and gain correction. It also properly selects and performs the following processes: recognition of X-ray irradiation field, gray scale transform adapted to image diagnosis, reduction of grid stripes, frequency processing (edge emphasis, emphasis of portions lower in contrast and sharpness), and addition of signals. An image processing circuit processes the digital signal from the reading circuit 6 using FPGA (Field Programmable Gate Array), or SOC (System On a Chip). This structure does not cause a delaying and therefore suitable for the moving image since the signal processing is performed within the electronic cassette. And, the image processing circuit including the FPGA or SOC adapted to a necessary image processing function can be selected for being connected. Accordingly, since unnecessary image processing circuit is not connected, power supplying to such unnecessary image processing circuit can be saved. The power consumption can be reduced. For the still image radiographing, real time monitoring is not always necessary. Accordingly, the fundamental structure thereof does not include the image processing circuit. In case of such structure, the digital signal form the reading circuit 6 is directly outputted to an external. However, even in such case, the image processing circuit provided with FPGA and SOC having minimum function such as a fixed pattern noise correction or the like may be provided therein in the still image radiographing. Because, such minimum function structure is in general relatively low power consumption one. If the image processing circuit has a function to output signals to the outside, the circuit can be connected to the external display to display X-ray images. In such structure, since it is unnecessary to output the signal to the external image processing circuit, high speed moving image can be performed.

The connection of the display to the electronic cassette 1 permits confirming X-ray images in real time at a place of X-ray radiographing. If the electronic cassette 1 is configured so as to house the display therein, a portion of the casing corresponding to the additional function modules 21 is made of transparent material. Data reduced by a function of adding pixel of the image processing circuit is sent to the display to be displayed thereon in real time. An opaque partitioning wall may be provided between the sensor panel 2 and the additional function modules 21 to prevent picture quality from degrading by irradiating the sensor panel 2 with light of the display. The connection of the display to the electronic cassette 1 allows radiographing in real time.

The connection of the wireless communication circuit to the electronic cassette 1 allows transmitting X-ray radiographed signals to an external computer. The external computer performs a predetermined process and images are displayed on an external display. If the foregoing image processing circuit is connected to the electronic cassette 1 at that point, signals can be directly transmitted to the external display to be displayed thereon. This makes it easier to carry the cassette and to confirm images. If an object of radiography has an IC tag with an individual identification signal, the X-ray radiographed signal can be provided with an individual identification data, which allows clearly identifying the object with the image. Particularly in the moving image radiographing, the connection of the wireless communication circuit to the electronic cassette 1 further enables long-time X-ray radiographing irrespective of the capacity of the storage device.

The connection of the light source to the electronic cassette 1 allows the optical reset of the sensor panel 2. In this case, since the sensor panel 2 is irradiated with light, a light guide plate is arranged in advance on the side opposite to the X-ray incident side of the sensor panel 2. The light source is connected to irradiate the panel with light, further adding an optical reset function to restrain change in picture quality due to changing of sensor characteristics with time.

The connection of the cooling element to the electronic cassette 1 can suppress a rise in temperature inside the electronic cassette 1 due to heat generated during the operation of one of the driving circuit 5 and the reading circuit 6. This suppresses change in characteristics due to change in temperature of the sensor panel 2. Accordingly, change in picture quality can be suppressed. The connection of the cooling element to the electronic cassette 1 in the moving image radiographing, in particular, can provide an image with less degrading with time if a continuous X-ray radiographing is performed for a long time. For this reason, a time period is extended during which images can be continuously radiographed with the power supply turned on, irrespective of the radiographing mode such as still image radiographing or moving image radiographing.

The connection of the heat radiator plate to the electronic cassette 1 produces the same effect as that of the cooling element.

The connection of the battery to the electronic cassette 1 allows extending the operating time of the electronic cassette 1. If other additional function modules mentioned above are connected, consumption power is increased, so that it is desirable to connect the battery to the electronic cassette at the same time. The connection of the cooling element or the heat radiator plate and the battery as the additional function module forms the minimum configuration which is best suited for light weight and long-time moving image radiographing. This is because the configuration can maintain the optimum operating temperature in the device for a long time. And, the electronic cassette 1 achieves high speed moving image radiographing by further adding thereto a reading circuit. In case of adding the reading circuit, though the power consumption and heat generation increase, since the cooling element or heat radiation plate and battery are already connected thereto, long time operation of the apparatus and maintaining a suitable operation temperature are achieved.

The aforementioned additional function modules can be provided with a control circuit. This enables bilateral communication with the control circuit 7 in the electronic cassette 1 and distributed processing, increasing a processing speed.

The electronic cassette 1 can be provided with a recognition unit for recognizing the connection of the above additional function modules and kinds thereof. For example, an optical sensor, magnetic sensor and switch are used as the recognition unit.

Figure 2:
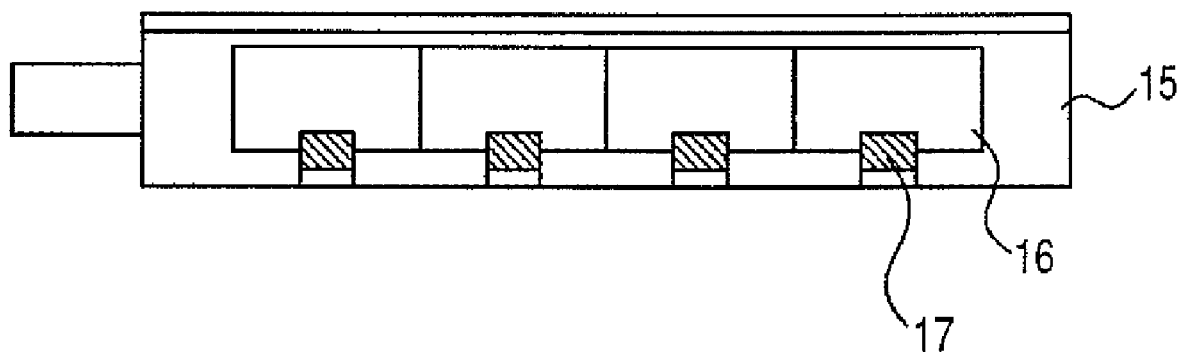
FIG. 2 is a side view of the X-ray detecting apparatus in the first embodiment of the present invention.

FIG. 2 is a side view illustrating the structure of the electronic cassette type of X-ray detecting apparatus in the present embodiment. As illustrated in FIG. 2, a lid 16 of an insertion portion for the additional function module 21 is fixed to the casing 15 by a lock mechanism 17. By means of such configuration, the additional function module 21 can be readily held, to maintain a condition within the apparatus.

Figure 5:
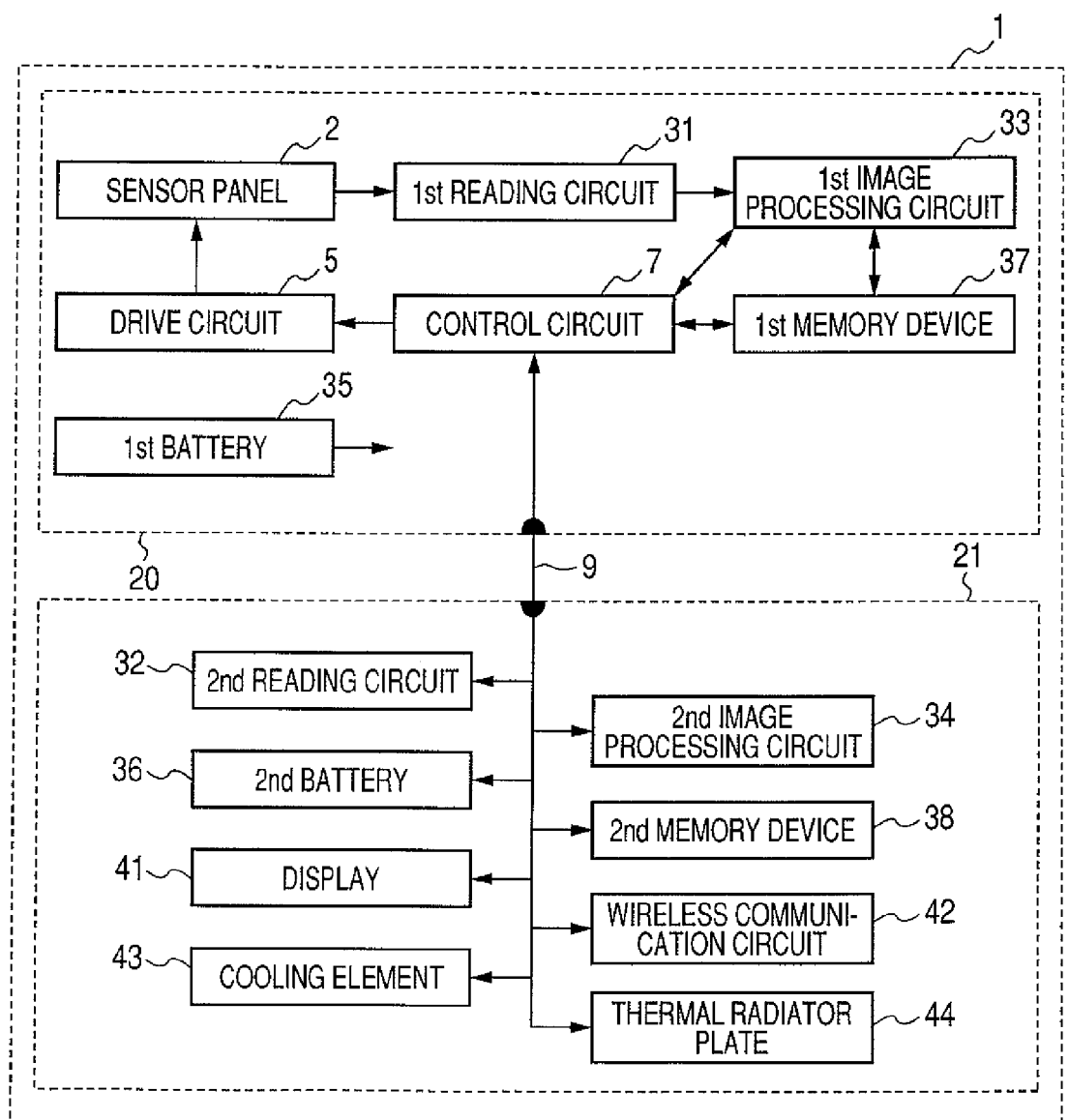
FIG. 5 is a block diagram showing an example of a structure of X-ray radiation detection apparatus according to a first embodiment of the present invention.

FIG. 5 is a block diagram showing an example of a structure of X-ray radiation detection apparatus according to a first embodiment of the present invention.

In the electronic cassette 1, the fundamental structure 20 and the additional function module 21 are connected through a connecting terminal 9.

The fundamental structure 20 comprises a sensor pane 12, a first reading circuit 31, a first image processing circuit 33, a drive circuit 5, a control circuit 7, a first memory device 37, a first battery 35 and a connecting terminal 9. And, an additional function module 21 connected to the fundamental structure 20 comprises a second reading circuit 32, a second image processing circuit 34, a second battery 36, a second memory device 38, a display 41, a wireless communication circuit 42, a cooling element 43 and a thermal radiator plate 44. Needless to say, it is not always necessary to connect all of the elements of the additional function module 21 when the electronic cassette suitable for the moving image radiographing is to be provided.

In case of the X-ray radiographing using the electronic cassette 1, firstly, a signal (analog) converted from X-ray is read out through the sensor panel 2, the drive circuit 5, the first reading circuit 31 and the control circuit 7. The first reading circuit 31 converts the analog signal transferred from the sensor panel 2 into a digital signal. The digital signal is subjected to an image processing meeting the minimum requirements as the occasion demands. And, the digital signal is stored in the first memory. A power necessary for an operation of the fundamental structure 20 is supplied form the first battery 35.

Wherein, the second reading circuit 32 conducts a processing of parallel conversion of the analog signal divisionally inputted from the first reading circuit 31 into the digital signal. For the signal conversion, the power consumption and heat generation quantity are made larger.

The second image processing circuit conducts a high level image processing rather than the first image processing circuit 33. Accordingly, the power consumption and heat generation quantity are made still larger.

The cooling element 43 cools a thermal generation portion such as the first and second image processing circuits 31 and 32. The thermal radiator plate 44 performs a heat radiation efficiently from an inside of the electronic cassette 1. Accordingly, even in case of connecting a module of a larger heat generation such as the signal processing circuit and the image processing circuit, a temperature suitable for the apparatus operation can be maintained.

The signal transfer between the first and second reading circuits 31 and 32 is not necessarily always through the control circuit 7. The signal transfer between the first and second image processing circuits 33 and 34 is not necessarily always through the control circuit 7. And, the signal transfer between the second memory device 38 and the first and second image processing circuits 33 and 34 is not always necessarily through the control circuit 7. With regard to the other additional modules such as the display and the wireless communication circuit, similarly, the communication to the circuits of the fundamental circuit 20 may be performed not through the control circuit 7.

Figure 6:
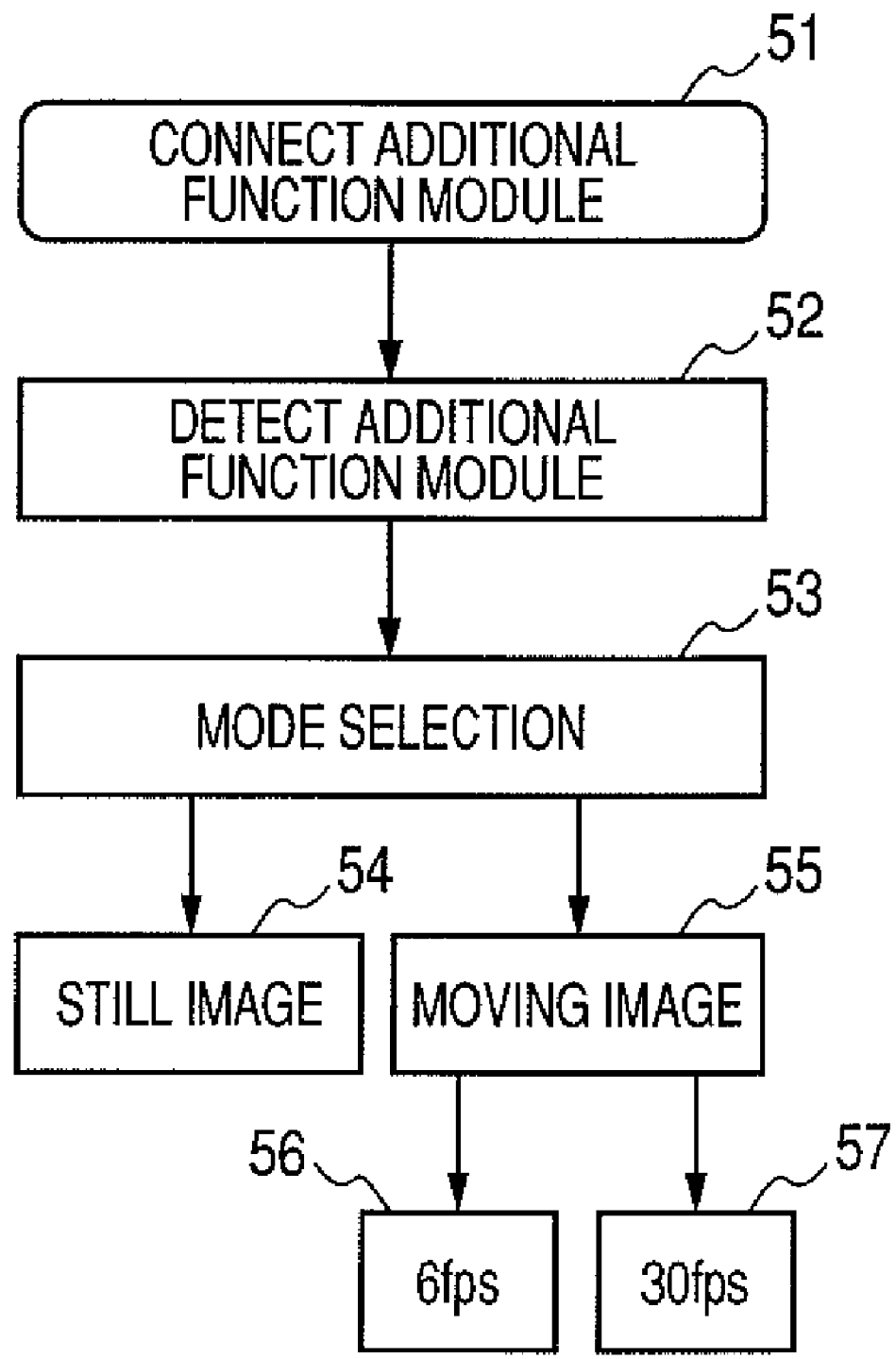
FIG. 6 is a flow chart showing an operation of X-ray detection apparatus according to the first embodiment of the present invention.

FIG. 6 is a flow chart showing an operation of X-ray detection apparatus according to the first embodiment of the present invention.

To the fundamental structure 20, the additional function module 21 is connected (step 51). The control circuit 7 detects the connection of the additional function module 21, and a kind of the additional function module 21 (step 52). The control circuit 7 operates as selection unit for changing a radiographing mode from a still image radiographing mode and a moving image radiographing mode into a selectable state. In this embodiment, the mode is set such that the moving image radiographing can be performed. And, a selection switch of the radiographing mode is turned on (step 53). The step 53 is executed only in a case that the radiographing mode change is necessary. That is, in case that the radiographing mode to be executed is the still image radiographing mode, without executing the step 53, the operation process proceeds to step 54. In case that the radiographing mode is to be changed automatically or manually from the still image radiographing mode, the operation process proceeds to step 55. At the step 55, speed 6 fps (frame/sec.) or 30 fps (frame/sec.) of the moving image radiographing mode is selected for providing a desirable moving image (step 56 or 57).

Second Embodiment

Figure 3:
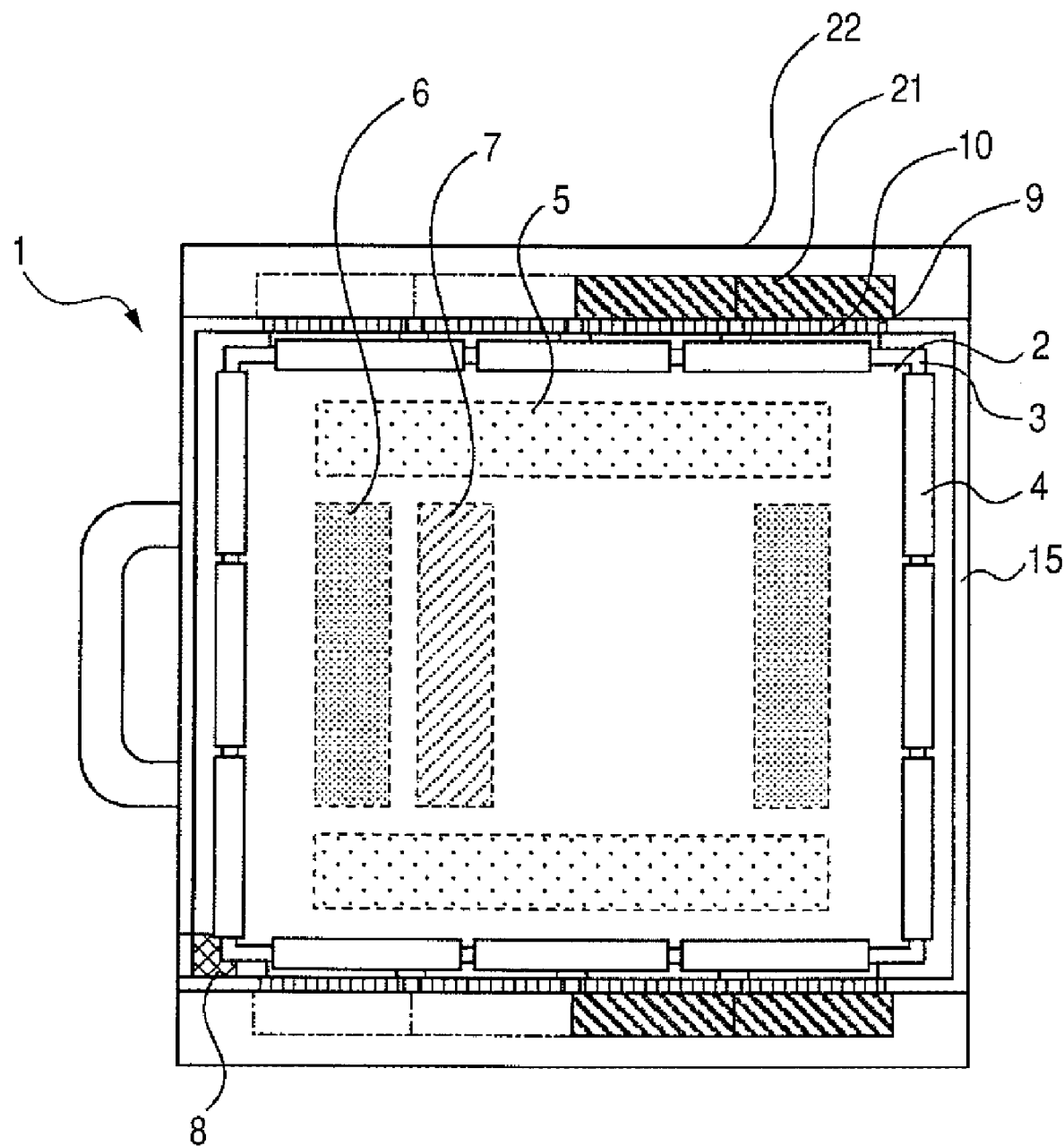
FIG. 3 is a cross section of an X-ray detecting apparatus in the second embodiment of the present invention.

FIG. 3 illustrates the electronic cassette in the present embodiment.

The point different from the first embodiment is that the additional function module 21 is connected to the outside of the electronic cassette 1 in the present embodiment.

This configuration can realize a lighter and smaller electronic cassette 1 if the additional function modules 21 are not connected thereto.

The additional function modules 21 are housed in the module casing 22. This configuration protects the additional function modules 21 against shock and makes it easy to handle the additional function modules 21. Alternatively, the additional function modules 21 may be individually connected to the electronic cassette 1.

Third Embodiment

Figure 4:
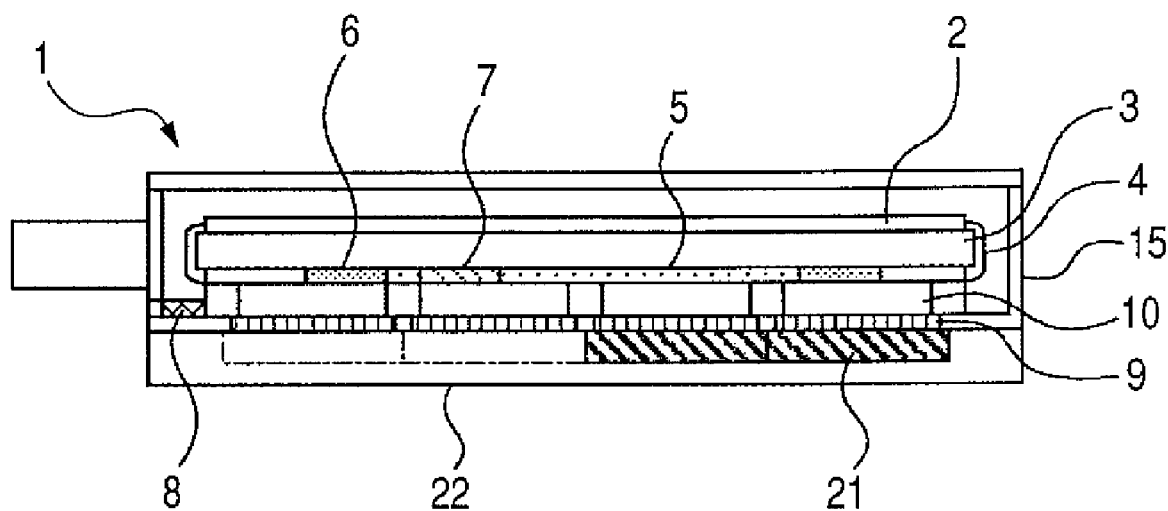
FIG. 4 is a side view of the X-ray detecting apparatus in the third embodiment of the present invention.

FIG. 4 illustrates the electronic cassette in the present embodiment.

The point different from the second embodiment is that the additional function modules 21 are connected to the side opposite to the X-ray incident side outside of the electronic cassette 1 in the present embodiment.

As is the case with the second embodiment, this configuration can also realize a lighter and smaller electronic cassette 1 if the additional function modules 21 are not connected thereto. In addition, even if the additional function modules 21 are connected, the surface area on the X-ray incident side of the electronic cassette 1 can be kept small, which makes it easy to handle.

The additional function modules 21 are housed in the module casing 22. This configuration protects the additional function modules 21 against shock and makes it easy to handle the additional function modules 21. Furthermore, a cooling element larger in surface area can be connected as the additional function module 21, further improving a cooling efficiency. Still furthermore, a larger-screen display can be connected as the additional function module 21, increasing accuracy in confirming images.

Alternatively, the additional function modules 21 may be individually connected to the electronic cassette 1.

In the above first to third embodiments, the modes are described in which the electronic cassette 1 with the basic configuration is connected to the additional function modules 21. In the present invention, additional function modules which are mobile and capable of adding other new functions can be connected to the electronic cassette 1, other than the above additional function modules. It is desirable that the electronic cassette 1 and the additional function modules 21 have a function such as the lock mechanism 17 illustrated in FIG. 2 to prevent the additional function modules 21 from coming off when connected.

In the above second and third embodiments, the modes are described in which the additional function modules 21 are connected to the outside of the electronic cassette 1, however, the electronic cassette 1 may be housed inside the module casing 22, for example, irrespective of the above modes.

With the sensor panel 2, a plurality of sensors capable of detecting radiation is arranged in two dimensions to form a sensor array. A direct conversion type of converting element such as, for example, a-Se for directly converting radiation into electric charge is used as the sensor. A photoelectric conversion element, for example, for indirectly converting radiation into electric charge is used as the sensor. In the photoelectric conversion element, a scintillator disposed on the radiation incident side of the photoelectric conversion element converts incident radiation into visible light and the photoelectric conversion element converts the visible light emitted from the scintillator into electric charge. Switching elements such as, for example, TFTs are connected to a plurality of sensors in the sensor array. Electric charges converted from radiation incident on the sensors are transferred by TFTs connected to the sensors. In particular, thallium with columnar crystal structure formed by evaporation or sodium doped CsI is used in the scintillator. As another example of a scintillator, a phosphor layer is used which is formed by coating and hardening phosphor powder with granular crystalline structure such as $Gd_2O_2S$ on binder resin such as polyester.

As many apparently widely different embodiments of the present invention can be made without departing from the spirit and scope thereof, it is to be understood that the invention is not limited to the specific embodiments thereof except as defined in the claims.

What is claimed is:

1. An electronic cassette type of radiation detection apparatus comprising:
a sensor array including a plurality of sensors for detecting incident radiation;
a light guide plate arranged on a side of the sensor array opposite to a radiation-incident side thereof; and
a connecting portion for connecting said radiation detection apparatus to one or more detachable additional function modules arranged at a side of the sensor array,
wherein the one or more additional function modules include a light source for irradiating the plurality of sensors with light for an optical reset, and the light source is included in the additional function modules arranged at the side of the sensor array.

2. The electronic cassette type of radiation detection apparatus according to claim 1, wherein, without connection with the detachable one or more additional function module(s), said radiation detection apparatus is capable only of operating in a still image radiographing mode.

3. The electronic cassette type of radiation detection apparatus according to claim 1, wherein a selection unit is provided for changing the radiographing mode from the still image radiographing mode or a moving image radiographing mode into a selectable state in response to connection of the electronic cassette type of radiation detection apparatus to the one or more additional function modules.

4. The electronic cassette type of radiation detection apparatus according to claim 1, wherein the radiographing mode is changed from the still image radiographing mode to the moving image radiographing mode, in response to connection of the electronic cassette type of radiation detection apparatus to the additional function module(s).

5. The radiation detection apparatus according to claim 1, wherein the one or more additional function modules include a storage device.

6. The radiation detection apparatus according to claim 1, wherein the one or more additional function modules include a signal processing circuit.

7. The radiation detection apparatus according to claim 1, wherein the one or more additional function modules include an image processing circuit.

8. The radiation detection apparatus according to claim 1, wherein the one or more additional function modules include a display for displaying an image derived by the moving image radiographing mode or the still image radiographing mode.

9. The radiation detection apparatus according to claim 8, wherein the display is connected to a side of the electronic cassette type of the radiation detecting apparatus opposite to a radiation incident side of the same apparatus.

10. The radiation detection apparatus according to claim 1, wherein the one or more additional function modules include a wireless communication circuit.

11. The radiation detection apparatus according to claim 1, wherein the one or more additional function modules include a cooling element or heat radiator plate.

12. The radiation detection apparatus according to claim 1, wherein the one or more additional function modules include a battery.

13. The electronic cassette type of radiation detection apparatus according to claim 1, further comprising a casing in which the sensor panel and the sensor array and the connecting portion are housed, wherein the one or more additional function modules are also housed in the casing.

14. The electronic cassette type of radiation detection apparatus according to claim 13, wherein the casing has a lock mechanism for holding the one or more additional function modules.

15. The radiation detection apparatus according to claim 1, wherein said radiation detection apparatus is connected to the one or more additional function modules through the connecting portion.

16. The electronic cassette type of radiation detection apparatus according to claim 1, wherein a battery is disposed inside of said radiation detection apparatus.

17. An electronic cassette type of radiation detection apparatus comprising:
 a sensor array including a plurality of sensors for detecting incident radiation;
 a connecting portion for connecting said radiation detection apparatus to one or more detachable additional function modules arranged at a side of the sensor array; and
 a first battery disposed inside said radiation detection apparatus,
 wherein, without connection with the one or more detachable additional function module(s), said radiation detection apparatus is capable only of operating in a still image radiographing mode,
 wherein a selection unit is provided for changing the radiographing mode from the still image radiographing mode or a moving image radiographing mode into a selectable state in response to connection of the one or more additional function modules, where at least a cooling element or a heat radiator plate and a second battery are ones of the additional function modules,
 wherein the one or more additional function modules include a light source for irradiating the plurality of sensors with light for an optical reset, and the light source is included in the additional function modules arranged at the side of the sensor array, and
 wherein the radiation detection apparatus further comprises a light guide plate arranged on a side opposite to a radiation-incident side of the sensor array.

* * * * *